Sept. 8, 1959 C. HARTGERINK Plant Pat. 1,862
ROSE PLANT
Filed Dec. 29, 1958
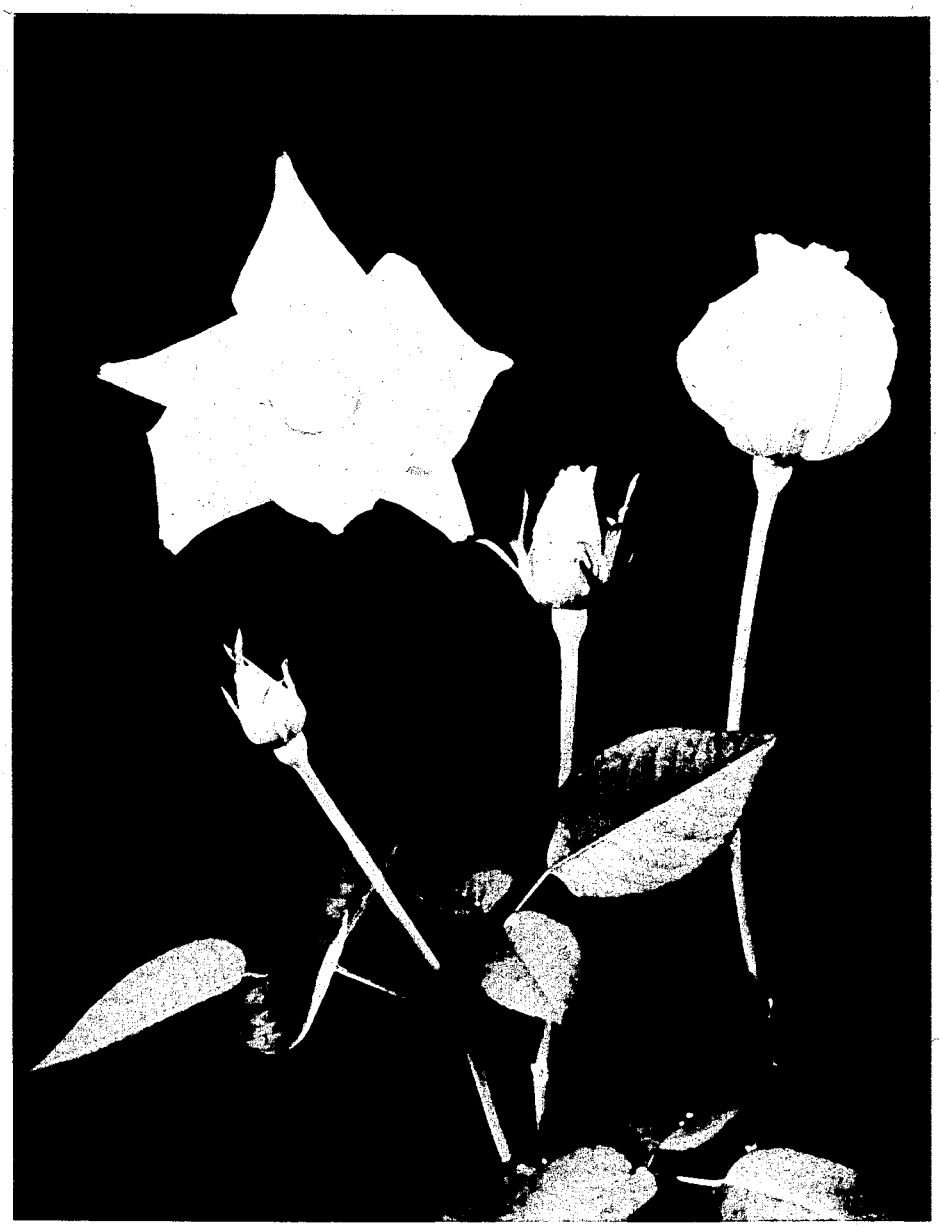
INVENTOR
Conrad Hartgerink
BY Robb & Robb
ATTORNEYS United States Patent Office Plant Pat. 1,862
Patented Sept. 8, 1959

1,862

ROSE PLANT

Conrad Hartgerink, West Los Angeles, Calif., assignor to Armacost & Royston, Inc., West Los Angeles, Calif., a corporation of California Application December 29, 1958, Serial No. 783,631

1 Claim. (Cl. 47—61)

The present invention relates to a new and distinct variety of rose plant of the hybrid tea class, which was originated by me by crossing the variety "White Ophelia" (unpatented) with an unnamed and unpatented seedling.

As the result of this breeding, I have produced a new rose variety which is particularly characterized as to novelty by the following unique combination of characteristics which are outstanding in the new variety and which distinguish it from its parents as well as from all other varieties of which I am aware:

(1) Luxuriant growth;
(2) Good flower production;
(3) Excellent form of the blooms;
(4) Large size of the blooms;
(5) A Pure White general color tonality of the blooms; and
(6) Good keeping qualities of the blooms when cut.

Asexual reproduction of my new variety by budding, as performed at West Los Angeles, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Koster's Color Guide, except where general color terms of ordinary dictionary significance are obvious:

Type: Half-hardy; tall; bush; greenhouse; for cut flowers.
Class: Hybrid tea.
Breeding: Seedling.
*Seed parent.*—"White Ophelia."
*Pollen parent.*—An unnamed seedling.
Propagation: Holds its distinguishing characteristics through succeeding propagations by budding.

*Flower*

Locality where grown and observed: West Los Angeles, California.
Flowers borne: Singly; on strong stems of medium length.
Quantity of bloom: Moderate, in greenhouse.
Continuity: Continuous.
Fragrance: Slight.
Bud:
*Peduncle.*—Long; heavy; erect; with few prickles. Color—light green.
*Before calyx breaks.*—Size—medium. Form—long; pointed; with a conspicuous neck; with foliaceous appendages on the surface of the bud; with much-cut foliaceous parts extending beyond the tip of the bud equal to ¼ or more of its length. Color—Pure White, Plate 1.
*As calyx breaks.*—Color—Creamy White, Plate 2.
*As first petal opens.*—Size—medium. Form—long; pointed. Color: outside—Pure White, Plate 1; inside—Creamy White, Plate 2.
*Opening.*—Opens up well.

Bloom:
*Size (when fully open).*—Large; from 4½ inches to 5 inches.
*Petalage.*—Double (no stamens showing); from 20 to 22 petals; arranged regularly.
*Form.*—High-centered at first, but becoming globular; petals being at first tightly cupped and rolled inward, but later becoming loosely cupped and rolled outward at maturity.
Petals:
*Texture.*—Thick; soft; with both inside and outside velvety.
*Shape.*—Outside—lanceolate. Intermediate—lanceolate. Inside—lanceolate.

This descripiton of a newly opened flower was made from a rose grown in a greenhouse in the month of October at West Los Angeles, California:

*Color.*—Outer petal: outside surface—Pure White, Plate 1; inside surface—Pure White, Plate 1. Intermediate petal: outside surface—Pure White, Plate 1; inside surface—Pure White, Plate 1. Inner petal: outside surface—Creamy White, Plate 2; inside surface—Creamy White, Plate 2.

This description was made from a rose that was open for 3 days in a greenhouse in the month of October at West Los Angeles, California:

*Color.*—Outer petal: outside surface—Pure White, Plate 1; inside surface—Pure White, Plate 1. Inner petal: outside surface—Creamy White, Plate 2; inside surface—Creamy White, Plate 2.
*General color effect.*—Newly opened flower—Pure White, Plate 1. 3-days open—Pure White, Plate 1.
*Behavior.*—Drop off cleanly.
*Flower longevity.*—Cut roses grown in a greenhouse and kept at living-room temperature—5 days in October.

Reproductive organs

Stamens: Medium number; arranged irregularly about pistils; mixed with petaloids; tucked in calyx. Color—yellow.
Filaments: Medium length; most with anthers. Color—yellow.
Anthers: Medium size; open at various times. Color—yellow.
Pollen. Moderate. Color—yellow.
Pistils: medium number.
Styles: Uneven length; medium length; medium caliper; loosely bunched.
Stigma: Color—red.
Ovaries: Some protruding from calyx.
Hips: Globular; with conspicuous and pear-shaped neck; smooth; walls thick and fleshy. Color—yellow.
Sepals: Permanent; long; spear-shaped; recurved. Color—brown.
Seeds: Many; medium size.

*Plant*

Foliage:
*Leaves.*—Compound of 3 to 5 leaflets; moderately abundant; moderately large; heavy; leathery.
*Leaflets.*—Shape—ovoid, with apex acute. Base—obtuse. Margin—irregularly serrate.
*Color.*—Mature: upper surface—Holly Green, Plate 82; under surface—Sage Green, Plate 78. Young: upper surface—Boxwood Green, Plate 79. under surface—Olive Green, Plate 84.

*Rachis (the supporting stem of the compound leaf).*—Medium caliper. Upper side—smooth; grooved. Under side—moderately smooth.

*Stipules.*—Medium length; narrow; with short points turning out at an angle of less than 45°; recurved toward the stem.

*Disease and insect resistance.*—Good resistance to mildew and insects, without any evidence of blackspot, as determined from comparison with other varieties grown under comparable cultural conditions at West Los Angeles, California.

Growth:

*Habit.*—Upright.

*Growth.*—Vigorous.

*Canes.*—Medium heavy.

*Main stems.* — Bright. Color — Boxwood Green, Plate 79. Thorns—few; hooked downward; with short base. Prickles—few; color—brown. Hairs—none.

*Branches.*—Bright. Color—Boxwood Green, Plate 79. Thorns—few; hooked downward; with short base. Prickles—none. Hairs—none.

*New shoots.*—Color: upper surface—Van Dyck Brown, Plate 96; under surface—Bistre, Plate 93. Thorns—few; hooked downward; with short base. Prickles—few; color—reddish. Hairs—none.

I claim:

A new and distinct variety of rose plant of the hybrid tea class, substantially as herein shown and described, characterized particularly as to novelty by the unique combination of luxuriant growth, good flower production, excellent form and large size of the blooms, a Pure White general color tonality of the blooms, and good keeping qualities of the blooms when cut.

No references cited.